United States Patent [19]
Kajiyama et al.

[11] Patent Number: 5,226,910
[45] Date of Patent: Jul. 13, 1993

[54] SURGICAL CUTTER

[75] Inventors: Hiroshi Kajiyama; Kunihiro Hayashi; Yoshihiko Hanamura, all of Tokyo, Japan

[73] Assignee: Kabushiki Kaisha TOPCON, Tokyo, Japan

[21] Appl. No.: 896,923

[22] Filed: Jun. 11, 1992

Related U.S. Application Data

[63] Continuation of Ser. No. 545,713, Jun. 29, 1990, abandoned.

[30] Foreign Application Priority Data

Jul. 5, 1989 [JP] Japan ................. 1-171972

[51] Int. Cl.$^5$ ............................................. A61B 17/32
[52] U.S. Cl. ............................................. 606/171; 604/22
[58] Field of Search ................ 606/170, 171; 128/751, 128/752, 755; 604/22; 30/241

[56] References Cited

U.S. PATENT DOCUMENTS

| | | | |
|---|---|---|---|
| 3,289,669 | 12/1966 | Dwyer et al. ................ | 128/752 |
| 3,815,604 | 6/1974 | O'Malley et al. ............ | 606/171 X |
| 4,210,146 | 7/1980 | Banko .......................... | 606/171 |
| 4,513,745 | 4/1985 | Amoils ........................ | 606/171 |
| 4,653,496 | 3/1987 | Bundy et al. ................ | 128/751 X |
| 4,696,298 | 9/1987 | Higgins et al. .............. | 606/171 |
| 4,819,635 | 4/1989 | Shapiro ....................... | 604/22 |
| 4,846,192 | 7/1989 | MacDonald ................. | 606/171 X |

FOREIGN PATENT DOCUMENTS 1519656 11/1989 U.S.S.R. ................. 128/751

Primary Examiner—Michael H. Thaler
Attorney, Agent, or Firm—Foley & Lardner

[57] ABSTRACT

A surgical cutting instrument which comprises an outer tubular member having a closed distal end closed and also having an aperture defined therein adjacent to the closed distal end which is in communication with the hollow of the outer tubular member and an inner tubular member having an open distal end which is slidably disposed in the outer tubular member such that the inner tubular member slides along its longitudinal axis first and second positions. The distal end of the inner tube has also has a scraper region defined therein. The scraper region is curled so as to represent a curved shape corresponding to a portion of a circle having a diameter greater than the outer diameter of the inner tubular member, so that when the inner tubular member is moved within the outer tubular member, the curled scraper region can be forcibly brought into sliding contact with an inner peripheral surface of the outer tubular member. Therefore, during the movement of the inner tubular member from the first position towards the second position relative to the outer tubular member, the curled scraper region is moved past the aperture in the outer tubular member to cut a tissue entering into the outer tubular member through the aperture.

3 Claims, 4 Drawing Sheets

SURGICAL CUTTER

This application is a continuation of application Ser. No. 07/545,713, filed Jun. 29, 1990, now abandoned.

BACKGROUND OF THE INVENTION

The present invention generally relates to an in vivo surgical instrument and, more particularly, to a surgical instrument suited, but not exclusively limited thereto, for use in an ophthalmic surgical operation for the removal of the diseased vitreous.

It is well known that in ophthalmic surgical operations a surgical cutting instrument is utilized to remove the diseased vitreous. According to the state of art, the surgical cutting instrument is available in various types. One surgical cutting instrument comprises an outer tube having a distal end, and an inner tube having a distal end which is axially slidably inserted in the outer tube. The outer tube has a perforation defined therein at a position axially and inwardly of the distal end thereof. The distal end of the inner tube, and a peripheral lip region, defining the aperture in the outer tube, cooperate with each other to provide a scissor action when the inner tube is axially moved relative to the outer tube.

In order to improve cutting performance, the inner tube should be designed so as to move along the curved outer tube so that, during the axial movement of the inner tube relative to the outer tube, an outer peripheral surface of the inner tube and an inner peripheral surface of the outer tube can fit into one another as perfectly as possible.

Another known surgical cutting instrument similarly comprises an outer tube having a distal end and a perforation defined therein adjacent the distal end thereof, and an inner tube having a distal end which is axially slidably inserted in the outer tube. In order to improve cutting performance, the distal end of the inner tube is flared axially outwardly so that the axially outwardly flared distal end of the inner tube and a peripheral lip region defining the aperture in the outer tube cooperate with each other to provide a scissor action when the inner tube is axially moved relative to the outer tube.

It has, however, been found that any one of the above discussed prior art surgical cutting instruments have their own problems. Specifically, in the surgical cutting instrument utilizing the outer tube curved so as to permit the inner tube to slide in tight contact with the inner peripheral surface of the outer tube, a difficulty has often been encountered in making an access to and withdrawal from the site of surgical operation because of the curved feature. Also, the employment of the curved feature in the outer tube obviously results in an enlargement of the aperture defined therein and, therefore, during the access to and the withdrawal from the site of surgical operation, a texture adjacent the site of surgical operation may be inadvertently scratched.

On the other hand, in the prior art surgical cutting instrument wherein the distal end of the inner tube is flared axially outwardly, the axial outwardly flared distal end of the inner tube serves as a movable blade which cooperates with the peripheral lip region of the aperture in the outer tube which serves as a stationary blade. Considering that the axially outwardly flared feature in the distal end of the inner tube has been employed for the purpose of providing a sharp cutting action during the relative movement of the inner tube within the outer tube, the repetition of this relative movement brings about a quick wear of the movable blade resulting not only in a reduction in cutting performance, but also in a reduction in the lifetime of the surgical cutting instrument.

Accordingly, the present invention has been devised to provide an improved surgical cutting instrument capable of exhibiting a sharp cutting performance for a substantially prolonged period of use.

Another important object of the present invention is to provide an improved surgical cutting instrument of the type referred to above, which is readily and easily accessible to a site of surgical operation in order to remove an affected tissue without substantially causing retraumatization of the surgical site.

SUMMARY OF THE INVENTION

In order to accomplish these and other objects, the present invention provides a surgical cutting instrument which comprises an outer tubular member having a distal end closed and also having an aperture defined therein adjacent the distal end in communication with the hollow of the outer tubular member, and an inner tubular member having a distal end opened and accommodated within the outer tubular member for axial sliding movement between first and second positions. The distal end of the inner tube has a longitudinal axis and also has a scraper region defined therein. This scraper region is curled so as to represent a curved shape corresponding to a portion of the circle of a diameter greater than the outer diameter of the inner tubular member, so that, when the inner tubular member is moved within the outer tubular member, the curled scraper region can be forcibly brought into sliding contact with an inner peripheral surface of the outer tubular member. Therefore, during the movement of the inner tubular member from the first position towards the second position relative to the outer tubular member, the curled scraper region is moved past the aperture in the outer tubular member to cut a tissue entering into the outer tubular member through the aperture.

Preferably, the scraper region may be defined by a circumferential cutout groove defined in the inner tubular member so as to extend in a direction circumferentially of the inner tubular member, and an axial cutout groove defined in the inner tubular member so as to extend in a direction parallel to the longitudinal axis thereof from a circumferential edge of the distal end of the inner tubular member.

Alternatively, the scraper region may extend generally helically with respect to the longitudinal axis of the inner tubular member.

According to the present invention, since the scraper region defined at the distal end of the inner tube is so curled as to represent a curved shape occupying a portion of the circle of a diameter greater than the outer diameter of the inner tubular member, the curled scraper region cooperates with the inner peripheral surface of the outer tube during the relative axial movement of the inner tube within the outer tube to cut the affected tissue while the curled scraper is elastically urged to tightly contact the inner peripheral surface of the outer tube, thus exhibiting an enhanced cutting performance.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, the scope of which is to be determined solely by the appended claims. In the accompanying drawings, like reference numerals are used to denote like parts throughout the several views, and:

DETAILED DESCRIPTION OF THE EMBODIMENTS

Figure 1:
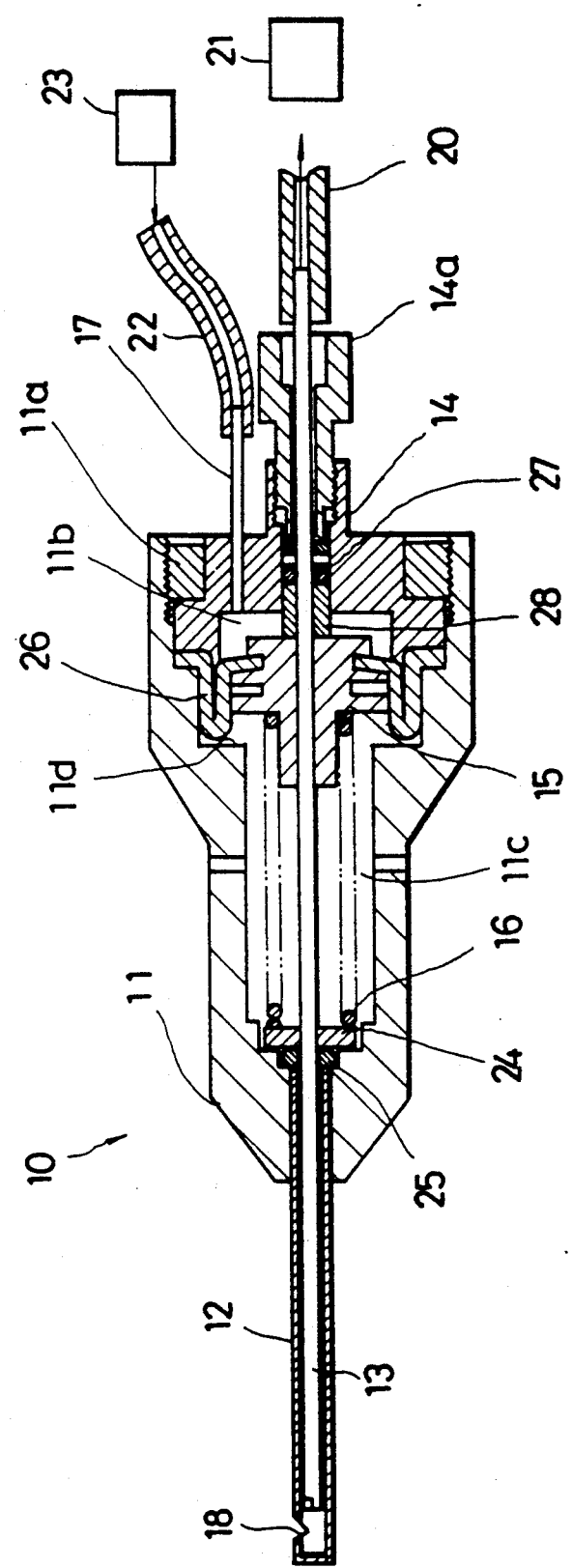
FIG. 1 is a longitudinal sectional view of an ophthalmic surgical cutting instrument embodying the present invention.

Referring first to FIG,. 1, there is shown a general construction of an in vivo ophthalmic surgical instrument to which the present invention pertains. The ophthalmic surgical instrument is generally identified by 10 and comprises a generally tubular casing 11 which also serves as a grip accessible to the hand of a surgeon, an outer tube 12 extending axially outwardly from one end of the casing 11, and an inner tube 13 disposed within the outer 12 and slidable along its axis. The casing 11 has distal and proximal ends opposite to each other and also has an axial cavity defined therein, and openings at the distal and proximal ends. The opening at the proximal end of the casing 11 is closed by a rear end lid 14 which is inserted a distance into the cavity and firmly retained in position by means of an annular adjustment ring 11a threaded thereinto. The cavity in the casing 11 is divided into rear and front compartments 11b and 11c by a piston member 15 and an annular diaphragm 26 having an inner peripheral edge rigidly secured to the piston member 15 and an outer peripheral edge firmly clamped between the rear end lid 14 and a shoulder which extends radially inwardly from an inner peripheral surface of the casing 11.

The rear compartment 11b within the cavity in the casing 11 is delimited between the diaphragm 26, the piston member 15 and the rear and lid 14 and is in communication with a source of compressed air 23 through an air pipe 17 and a flexible air tube 22.

The piston member 15 is movable axially within the casing 11 between retracted and projected positions and is normally biased to the retracted position by the action of a biasing spring 16. This biasing spring 16 is operatively accommodated within the front compartment 11c and is interposed between the piston member 15 and an annular shoulder extending radially inwardly from the inner peripheral surface of the casing 11. One end of the biasing spring 16 which is adjacent the distal end of the casing 11, is brought into contact with the annular shoulder through an annular O-ring retainer 24 serving to retain an O-ring 25 in the position as will be described later. It is to be noted that the source of compressed air 23 is of a type capable of supplying the compressed air in pulsating fashion, that is, pulses of compressed air, and is therefore to be understood as including a pumping mechanism for pulsating the compressed air.

In the construction so far described, it will readily be understood that, when a single pulse of compressed air is introduced into the rear compartment 11b of the casing 11, the piston member 15 is driven from the retracted position, as shown in FIG. 1, towards the projected position against the biasing spring 16, and that, as the pulses of compressed air are supplied into the rear compartment 11b in the casing 11, the piston member 15 is reciprocatingly moved between the projected and retracted positions at a frequency corresponding to the number and frequency of the pulses of the compressed air.

The outer tube 12 has a closed distal end and an open proximal end opposite to the closed distal end thereof, and is secured to the casing 11 with the proximal end tightly and fixedly inserted into the distal end of the casing 11 in alignment with the cavity in the casing 11. The outer tube 12 has a perforation 18 defined therein at a location adjacent the closed distal end thereof which is in communication with the interior of the outer tube 12.

The inner tube 13 has open distal and proximal ends and is partially disposed within the outer tube 12 and partially disposed within the cavity in the casing 11, and extends completely through the piston member 15 and the rear end lid 14. The distal end is situated within the outer tube 12 and with the proximal end situated outside the casing 11. An annular gap between the proximal end of the outer tube 12 and a substantially intermediate portion of the inner tube 13, which is adjacent to the O-ring retainer 24, is completely sealed off by the O-ring 25 which is held in position the annular gap by O-ring retainer 24, and accordingly, no air from within the front compartment 11c in the casing 11 can enter the outer tube 12.

Figure 2:
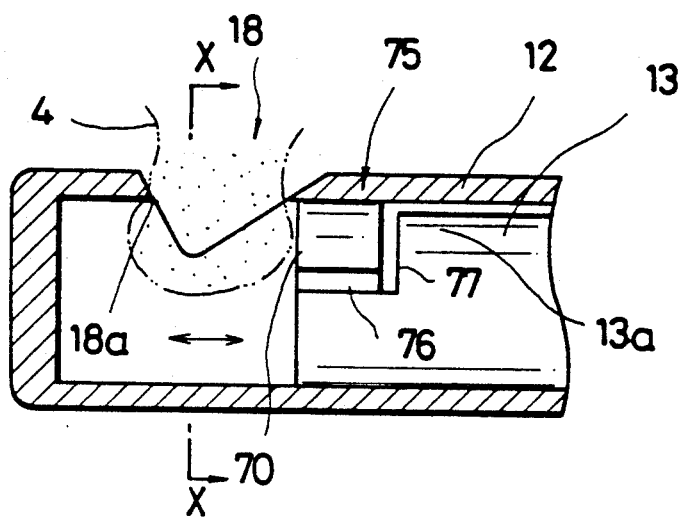
FIG. 2 is a longitudinal sectional view, on an enlarged scale, showing an essential portion of the surgical cutting instrument according to a first preferred embodiment of the present invention.

The proximal end of the inner tube 13 extending outwardly from the rear end lid 14 is in turn in communication with a source of vacuum 21, which may be a vacuum pump, through a suction piping 20. It is to be noted that a portion of the inner tube 13 extending completely through the piston member 15 is fixed thereto while another portion of the inner tube 13 extending completely through the rear end lid 14 is slidable relative thereto. It is also to be noted that the inner tube 13 and the piston member 15 are fixed relative to each other such that when the piston member 15 is held in the retracted position, as shown in FIG. 1, the open distal end of the inner tube 13 assumes a position which is spaced a distance axially inwardly from the closed distal end of the outer tube 13, and which is spaced a slight distance axially inwardly from the aperture 18 defined in the outer tube 12, as best shown in FIG. 2.

However, the home position of the inner tube 13 at which the open distal end thereof is positioned a slight distance axially inwardly from the aperture 18 in the outer tube 12, or the stroke of movement of the piston member 15 and hence that of the inner tube 13, can be adjusted. This is possible because an adjustment screw, through which the inner tube 13 loosely extends, is threaded into the rear end lid 14 in a coaxial relationship with the cavity in the casing 11 with an inner end thereof brought into engagement with the piston member 15 through an O-ring 27 and a stopper insert 28. The O-ring 27 prevents any possible escape of air from the rear compartment 11b to the outside through an annular gap which is present between the inner tube 13 and the rear end lid 14. Thus, it will readily be seen that, when the adjustment screw 14a is turned about the longitudinal axis of the casing 11, the piston member 15 can be moved axially within the cavity in the casing 11 to define the home position for the inner tube 13.

From the foregoing, it is clear that, when a single pulse of compressed air is introduced into the rear compartment 11b from the compressed air source 23, the piston member 15, together with the inner tube 13 can be axially driven, from the retracted position towards the projected position against the biasing spring 16, until the piston member 15 is brought into contact with an annular abutment shoulder extending radially inwardly from the casing as shown by 11d. At this time, a distal end portion of the inner tube 13 encompassed by the outer tube 12 is moved axially from the home position towards the closed distal end of the outer tube 12. When the supply of the pulse of compressed air into the rear compartment 11b is interrupted, the piston member 15 is moved back towards the retracted position by the action of the biasing spring 16 until the distal end portion of the inner tube 13 returns to the home position.

The open distal end of the inner tube 13 cooperates with a peripheral lip region defining the aperture 18 to provide a scissor action which cuts an affected tissue in the vitreous in a manner as will be described later. The affected tissue which is cut, is sucked into the inner tube 13 due to the source of vacuum 21, and is subsequentially removed out of the cutting instrument 10.

In accordance with the present invention, the distal end of the inner tube 13 is designed to have a curled scraper region which will now be described with reference to FIGS. 2 and 3.

Figure 3:
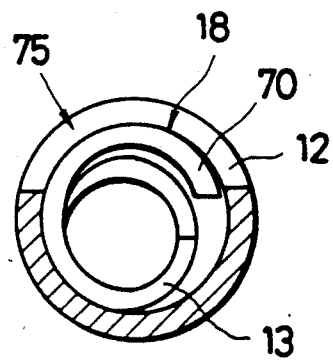
FIG. 3 is a cross-sectional view taken along the line X—X in FIG. 2.

Referring now to FIGS. 2 and 3, the curled scraper region is generally identified by 75 and is defined in the distal end of the inner tube 13 so as to include a portion 70 of the peripheral edge at the distal end of the inner tube 13. More specifically, the distal end of the inner tube 13 has a circumferential cutout groove or slot 77, defined therein so as to extend a certain angle in a direction circumferentially around the inner tube 13, and an axial cutout groove 76 also defined therein so as to extend axially inwardly of the inner tube 13 from the distal end edge thereof. The curled scraper region 75 has a generally arcuate shape when viewed in a direction axially of the tube assembly, and a generally rectangular shape when viewed in a direction perpendicular to the longitudinal axis of the tube assembly. The scraper region 75 has one end which is integral with the remainder 13a of the distal end of the inner tube 13, and an opposite free end, a substantially intermediate portion thereof extending in a direction circumferentially around the inner tube 13. This scraper region 75 acts as if it were a curled leaf spring, and is enlarged radially outwardly beyond the outer peripheral surface of the remainder 13a of the distal end of the inner tube 13, best shown in FIG. 3, scraper region 75 acts as a movable blade cooperating with an edge 18a of the peripheral lip region defining the aperture 18, the edge 18a serving as a stationary blade.

Because of the employment of the unique scraper region 75 in the distal end of the inner tube 13, as hereinbefore described, the inner tube 13 employed in the ophthalmic surgical instrument embodying the present invention may have an outer diameter greater than the inner diameter of the outer tube 12 by, for example, about 10%. Therefore, when the inner tube 13 is to be inserted into the outer tube 12, use is made of an appropriate jig to reduce the outer diameter of the inner tube 13 to allow it to be forcibly inserted into the outer tube 12.

When the inner tube 13 is so inserted onto the outer tube 12, the curled scraper region 75 is brought into sliding engagement with the inner peripheral surface of the outer tube 12 in a substantially surface-to-surface contact fashion, and therefore, it would not occur that only the portion 70 of the distal end edge of the inner tube 13 slides in contact with the inner peripheral surface of the outer tube 12. Because of the foregoing, no localized wear occurs in the portion 70 of the distal end edge of the inner tube 13, which would otherwise occur when only the portion 70 of the distal end edge of the inner tube 13 repeatedly slides in contact with the inner peripheral surface of the outer tube 12.

The operation of the ophthalmic surgical instrument embodying the present invention will now be described with particular reference to FIG. 1 to 3.

When the ophthalmic surgical instrument is in use during an ophthalmic surgical operation, and assuming that the vacuum source 21 is operated to draw air within the inner tube 13, an affected tissue 4 to be removed can be drawn into the outer tube 12 through the aperture 18 as shown by the phantom line in FIG. 2. The compressed air source 23 is subsequently operated to supply a pulse of compressed air into the rear compartment 11b to cause the piston member 15 to undergo a reciprocating motion between the retracted position and the projected position. As the inner tube 13 is axially moved with the piston member 15 from the retracted position towards the projected position against the biasing spring 16, the curled scraper region at the distal end of the inner tube 13 cooperates with the peripheral edge 18a of the perforation 18 to cut the affected tissue 4, and the cut affected tissue 4 is then drawn into the inner tube 13 and out of the instrument 10 towards the vacuum source 21 under the influence of a suction force created in the system.

Figure 4:
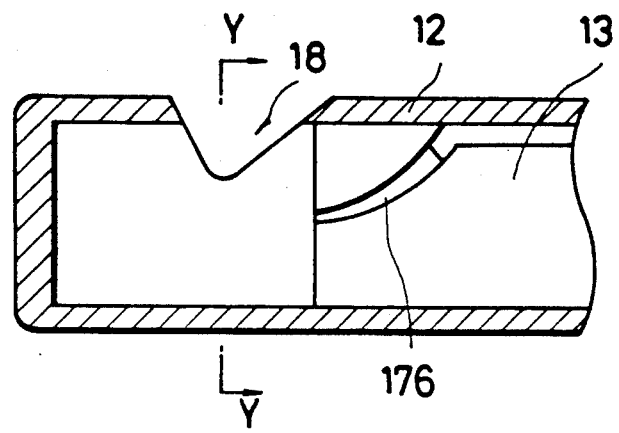
FIG. 4 is a view similar to FIG. 2, showing a second preferred embodiment of the present invention.
Figure 5:
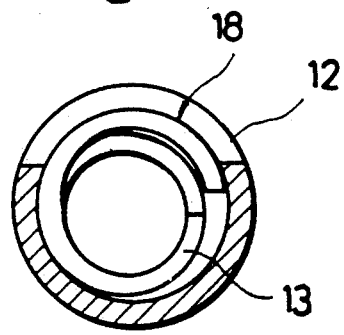
FIG. 5 is a cross-sectional view taken along the line Y—Y in FIG. 4.

In the foregoing embodiment of the present invention, the distal end of the inner tube 13 has been shown and described as having the circumferential and axial cutout grooves 76 and 77 to define the curled scraper region 75 thereon. However, in an embodiment shown in FIGS. 4 and 5, a single spiral cutout groove 176 is formed in the distal end of the inner tube 13 so as to extend substantially helically away from the distal end edge in a direction inwardly of the inner tube 13, leaving a similarly curled scraper region.

Figure 6:
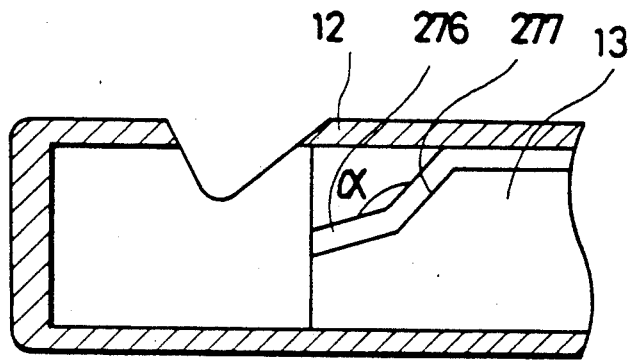
FIGS. 6 and 7 are views similar to FIGS. 2 and 3, respectively, showing third and fourth preferred embodiments of the present invention.

In an embodiment shown in FIG. 6, to define the scraper region in the inner tube adjacent the open distal end, a cutout groove 276, extending inwardly from the distal end edge of the inner tube, and a cutout groove 277 contiguous with and extending further inwardly from the cutout groove 276, form an angle α therebetween, which angle α may be, for example, 150°.

Figure 7:
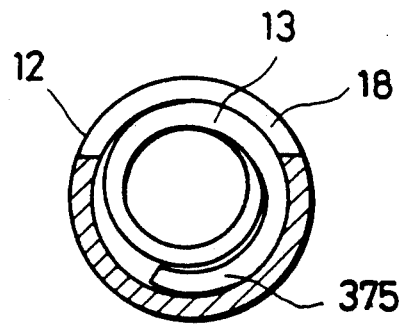

In an embodiment shown in FIG. 7, a curled scraper region 375, defined in the distal end of the inner tube 13 by the presence of a cutout groove, is positioned below and on one side remote from the aperture 18 defined in the outer tube 12.

Thus, according to the present invention, since the scraper region defined at the distal end of the inner tube is so curled as to represent a curved shape occupying a portion of the circle of a diameter greater than the outer diameter of the inner tubular member, the curled scraper region cooperates with the inner peripheral surface of the outer tube during the relative axial movement of the inner tube within the outer tube to cut the affected tissue, while the curled scraper is elastically urged to tightly contact the inner peripheral surface of the outer tube thereby exhibiting an enhanced cutting performance.

Since any one of the outer and inner tubes forming the surgical cutting instrument according to the present invention is not curved, an access of the surgical cutting instrument to and the withdrawal thereof from the site of surgical operation can readily be accomplished, without substantially giving rise to a problem of retraumatization.

Also, according to the present invention, the provision of the scraper region at the distal end of the inner tube enables a surface-to-surface contact to be attained between the inner tube and the outer tube with no substantial reduction in lifetime of the surgical cutting instrument due to wear.

Again, the curled scraper region employed in the embodiment shown in and described with reference to FIGS. 2 and 3 can readily and easily be formed by means of a readily available machining method, that is, by the employment of two linear cutout grooves that extend perpendicular to each other while assuring a tight sliding contact between it and the inner peripheral surface of the outer tube when the inner tube is inserted into the outer tube.

Yet, the substantially helically extending scraper region employed at the distal end of the inner tube makes it possible to assure a tight sliding contact between it and the inner peripheral surface of the outer tube.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. For example, the number of cutout grooves may not be limited to one or two, but may be more than two.

Also, the surgical cutting instrument according to the present invention, although shown and described as used in ophthalmic operation, can be equally used in any other application where a minute affected tissue is desired to be removed.

Accordingly, such changes and modifications are, unless they depart from the spirit and scope of the present invention as delivered from the claims annexed hereto, to be construed as included therein.

What is claimed is:

1. A surgical cutting instrument which comprises:
   an outer tubular member having a closed distal end and an aperture defined therein adjacent to said closed distal end which is in communication with the hollow of said outer tubular member; and
   an inner tubular member having an open distal end slidably disposed within said outer tubular member such that said inner tubular member slides along its longitudinal axis between first and second positions, said open distal end of said inner tubular member being, when said inner tubular member is moved from said first position to said second position, moved past said aperture in the outer tubular member;
   wherein said distal end of said inner tubular member has a scraper region defined therein, said scraper region being curled so as to represent a curved shape corresponding to a portion of a circle having a diameter greater than the outer diameter of said inner tubular member, said scraper region being, when the inner tubular member is moved within the outer tubular member, brought forcibly into contact with an inner peripheral surface of said outer tubular member, whereby during the movement of said inner tubular member from said first position towards said second position relative to said outer tubular member, a tissue entering into said outer tubular member through the aperture is cut by said scraper region, said scraper region having a first end integral with a portion of said distal end of said inner tubular member, a free end opposite to said first end, and an intermediate portion between said first and free ends extending in a substantially circumferential direction around said inner tubular member;
   wherein said scraper region is defined by a circumferential slot defined in said inner tubular member extending in a circumferential direction around said inner tubular member, and an axial slot defined in said inner tubular member extending in a parallel direction relative to said longitudinal axis and also extending from a circumferential edge of said distal end of said inner tubular member, said axial and circumferential slots intersecting with each other;
   wherein said circumferential slot extends over the full width of the aperture of said outer tubular member in its circumferential direction, and said scraper region is substantially rectangular when uncurled.

2. The instrument as claimed in claim 1, wherein said scraper region extends generally spirally with respect to the longitudinal axis of the inner tubular member.

3. A surgical cutting instrument which comprises:
   an outer tubular member having a distal end and an aperture defined therein which is in communication with the hollow of said outer tubular member; and
   an inner tubular member having a distal end which is slidably disposed within said outer tubular member such that said inner tubular member slides along its longitudinal axis between first and second positions;
   wherein said distal end of said inner tubular member has a scraper region defined therein such that during the movement of said inner tubular member from said first position towards said second position relative to said outer tubular member, a tissue entering into said outer tubular member through said aperture is cut by said scraper region, said scraper region having one end integral with a portion of said distal end of said inner tubular member, an opposite free end, and an intermediate portion between said one and free ends extending in a generally circumferential direction around said inner tubular member;
   wherein said scraper region is defined by a slot in said inner tubular member which extends in a circumferential direction around said inner tubular member, and an axial slot defined in said inner tubular member which extends in a parallel direction relative to said longitudinal axis from a circumferential edge of said distal end of said inner tubular member, said axial and circumferential slots intersecting with each other;
   wherein said circumferential slot extends over the full width of the aperture of said outer tubular member in its circumferential direction, and said scraper region is substantially rectangular when uncurled.

* * * * *